United States Patent
Zander et al.

(10) Patent No.: US 10,426,535 B2
(45) Date of Patent: Oct. 1, 2019

(54) SELF-HOLDING SCREW HEAD

(71) Applicant: Stryker European Holdings I, LLC, Kalamazoo, MI (US)

(72) Inventors: Nils Zander, Eckernförde (DE); Manfred Wieland, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 276 days.

(21) Appl. No.: 15/399,233

(22) Filed: Jan. 5, 2017

(65) Prior Publication Data

US 2018/0185076 A1    Jul. 5, 2018

(51) Int. Cl.
  *A61B 17/86* (2006.01)
  *A61B 17/88* (2006.01)

(52) U.S. Cl.
  CPC ........ *A61B 17/862* (2013.01); *A61B 17/8891* (2013.01); *A61B 17/8615* (2013.01)

(58) Field of Classification Search
  USPC .................................................. 606/305–308
  See application file for complete search history.

(56) References Cited

U.S. PATENT DOCUMENTS

| | | |
|---|---|---|
| 1,287,203 A | 12/1918 | Boyd |
| 1,364,478 A | 1/1921 | Boyd |
| 1,973,848 A | 9/1934 | Duffy |
| 2,704,170 A | 3/1955 | Ray |
| 4,478,113 A | 10/1984 | Berneiser |
| 4,541,139 A | 9/1985 | Jones et al. |
| 4,963,144 A | 10/1990 | Huene |
| 5,143,411 A | 9/1992 | Watts |
| RE34,467 E | 12/1993 | Reeves |
| 5,375,956 A | 12/1994 | Pennig |
| 5,536,127 A | 7/1996 | Pennig |

(Continued)

FOREIGN PATENT DOCUMENTS

| | | |
|---|---|---|
| EP | 0387392 A2 | 9/1990 |
| JP | H07505567 A | 6/1995 |

(Continued)

OTHER PUBLICATIONS

European Search Report from EP Application No. 2018150311, dated Mar. 21, 2018.

*Primary Examiner* — Matthew J Lawson
(74) *Attorney, Agent, or Firm* — Lerner, David, Littenberg, Krumholz & Mentlik, LLP

(57) ABSTRACT

A screw insertion system has a screw having a threaded shaft and a head. The head has a conically tapered outer surface, the taper increasing in distance from a central longitudinal axis of the screw from a free end of the head towards a larger diameter adjacent the connection between the head and the threaded shaft. The conically tapered head outer surface has preferably two helically extending partially rounded threads. The head has a drive element for engaging a driver. A tubular screw holder has an outer surface and internal bore extending between a leading end and a trailing end for receiving the screw. The leading end having a conically tapered inner threaded portion for engaging the conically tapered outer thread of the screw head. The tubular screw holder outer surface having a diameter less than or equal to the maximum diameter of the conically tapered head.

23 Claims, 9 Drawing Sheets

FIG. 1A

(56) References Cited

U.S. PATENT DOCUMENTS

| | | | |
|---|---|---|---|
| 5,737,981 A | 4/1998 | Hildebrand | |
| 6,017,177 A * | 1/2000 | Lanham | F16B 23/003 411/402 |
| 6,030,162 A | 2/2000 | Huebner | |
| 6,102,642 A * | 8/2000 | Kawashita | F16B 15/00 411/387.3 |
| 6,267,025 B1 | 7/2001 | Sand et al. | |
| 6,337,142 B2 | 1/2002 | Harder et al. | |
| 6,565,573 B1 | 5/2003 | Ferrante et al. | |
| 6,599,290 B2 | 7/2003 | Bailey et al. | |
| 7,476,228 B2 | 1/2009 | Abdou | |
| 7,798,755 B2 | 9/2010 | Tomm | |
| 7,887,547 B2 | 2/2011 | Campbell et al. | |
| 8,187,309 B2 | 5/2012 | Castaneda et al. | |
| 8,216,243 B2 | 7/2012 | Yevmenenko et al. | |
| 8,273,113 B2 | 9/2012 | Frenk et al. | |
| 8,460,349 B2 | 6/2013 | Frenk et al. | |
| 8,540,726 B2 | 9/2013 | Yevmenenko et al. | |
| 8,992,581 B2 | 3/2015 | Austin et al. | |
| 9,107,711 B2 | 8/2015 | Hainard | |
| 9,113,976 B2 | 8/2015 | Yevmenenko et al. | |
| 9,333,018 B2 | 5/2016 | Russell et al. | |
| 9,339,315 B2 | 5/2016 | Schwager et al. | |
| 9,387,022 B2 | 7/2016 | Koay et al. | |
| 2006/0025773 A1 | 2/2006 | Yevmenenko et al. | |
| 2006/0149264 A1 | 7/2006 | Castaneda et al. | |
| 2011/0060373 A1 * | 3/2011 | Russell | A61B 17/0401 606/304 |
| 2012/0022603 A1 * | 1/2012 | Kirschman | A61B 17/7064 606/305 |
| 2013/0011215 A1 * | 1/2013 | Wells | F16B 23/0007 411/402 |
| 2013/0226239 A1 | 8/2013 | Altarac et al. | |
| 2014/0018862 A1 * | 1/2014 | Koay | A61B 17/8057 606/281 |
| 2014/0114362 A1 * | 4/2014 | Giersch | A61B 17/68 606/304 |
| 2014/0236242 A1 | 8/2014 | Robinson | |
| 2014/0236245 A1 * | 8/2014 | Hainard | A61B 17/8057 606/291 |
| 2015/0362100 A1 | 12/2015 | Li et al. | |
| 2016/0151101 A1 | 6/2016 | Machida | |

FOREIGN PATENT DOCUMENTS

| | | |
|---|---|---|
| JP | 2011161583 A | 8/2011 |
| SU | 827050 A1 | 5/1981 |
| WO | 9420039 A1 | 9/1994 |

* cited by examiner

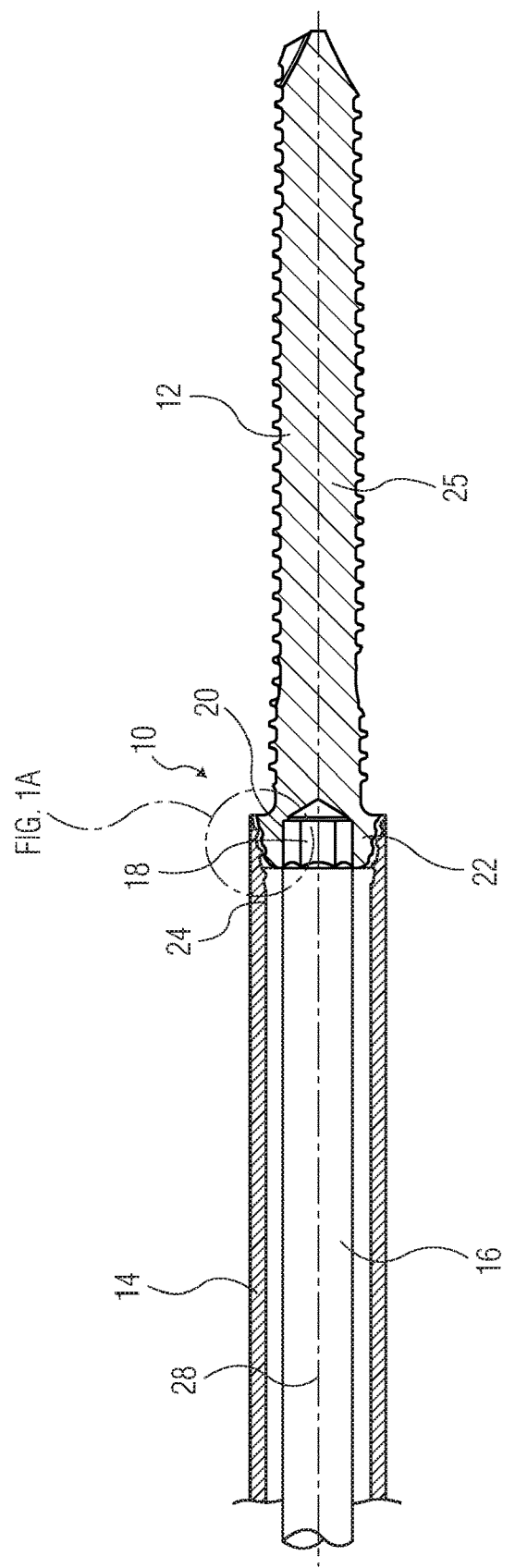

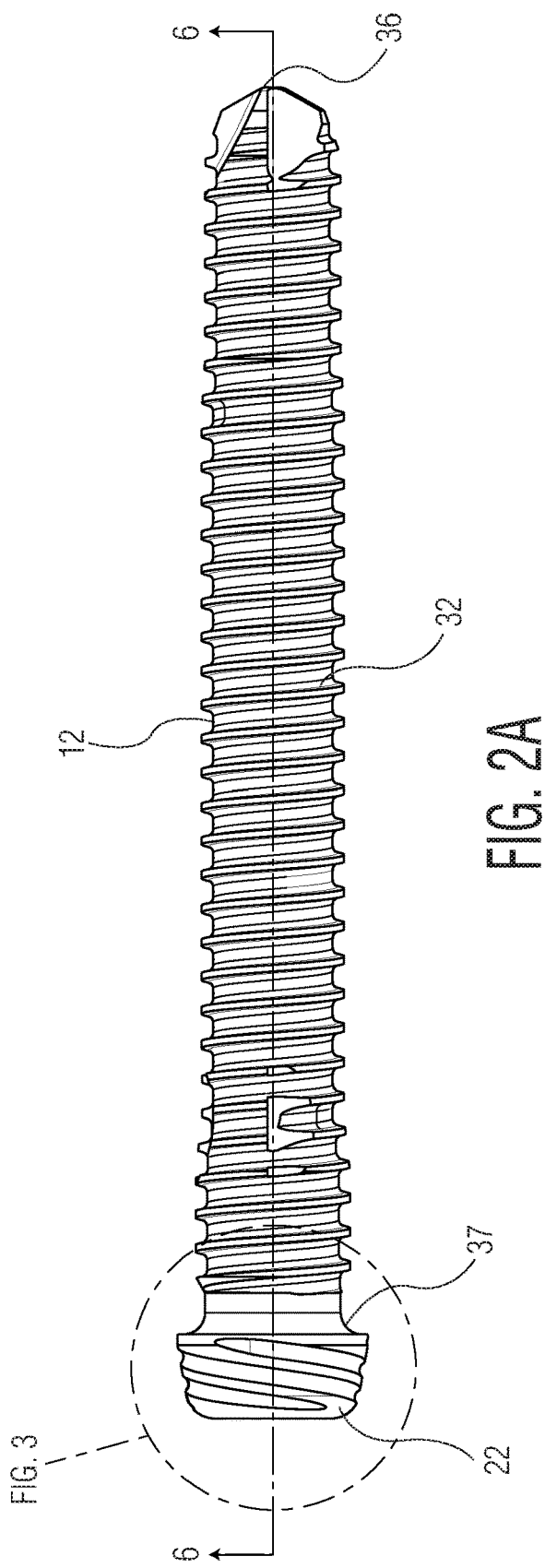

SELF-HOLDING SCREW HEAD

BACKGROUND OF THE INVENTION

During intramedullary nailing (IM) surgery it is of importance (especially in a freehand locking screw insertion procedure through large soft tissue coverage) to firmly fix the locking screw to the screw driver to avoid dropping and mis-angulating the locking screw. Present solutions are self-holding screw drivers which suffer from insufficient holding forces and susceptibility to deflexion caused by bending moment.

The screw head of the present invention offers a conical or spherical shape with an integrated external multiple, preferably triple thread (preferably a round thread and left-handed thread) which eases the adaptation of an external sleeve with internal thread. The external sleeve is guided/axially constrained by the screw driver shaft creating firm connection between sleeve and screw. Due to the conical/spherical design the outer diameter of the assembled screw head and sleeve construct does not exceed the maximum outer diameter of screw head and can be used through existing tissue protection sleeve systems. The transmission of the required torque remains utilizing the internal hex of the screw solely.

Compared to the already existing solutions the design of the present invention offers a more rigid connection under all loading conditions.

SUMMARY OF THE INVENTION

The present invention is a system having a screw with a threaded head, a tissue protection sleeve with an internal thread and a screw driver.

At the distal end of the screw is a threaded shaft having a first thread adapted to extend through the nail and engage the bone surrounding the IM canal. At the proximal end of the screw, there is formed on a screw head an outer thread, which extends preferably only a few millimeters along the screw head in the direction along the central axis of the screw. This second thread is a different kind of a thread compared with the first thread, since the second thread is adapted to engage with the tissue protection sleeve inner thread. To avoid negative interdependencies like irritations or lesions, between the second outer thread and tissue surrounding the bone, the outer contour of the windings are flattened or rounded so as to have a smooth contact area.

The second outer thread is adapted to be connected to an internal threaded tissue protection sleeve, wherein, the sleeve is supported at the proximal end of the screw by means of the second thread.

Furthermore, the proximal end of the screw includes an inner drive tool engagement portion. This means that the screw is coupled with a driver having a corresponding driving end. This driving end may be a hexagonal or a TORX® drive, wherein the driver may also be a wrench. It is noted that the driver may also be driven by a power source including an electric, pneumatic or other suitable mechanism.

The outer diameter of the second thread tapers outwardly from the central axis of the screw on moving along the head toward the distal end of the screw including the first thread. The second thread has a greater diameter than an outer diameter of the screw shaft. Therefore, a step will be formed between the second thread at the proximal end and the first thread of the shaft. According to that embodiment, the screw further comprises a distally facing annular surface between the second thread and the first thread shaft to provide a smooth junction or shoulder between the head second thread and the shaft first thread. Alternately, the distally facing surface may be formed as a part-spherical head portion with the part-spherical surface facing the distal end of the screw.

For the case of an implantation of a screw into a bone, a set or system for installation of the screw according to the invention comprises, beside the screw as described above, a driving tool adapted to engage with the inner tool engagement portion of the screw, and a hollow tissue protection sleeve adapted to engage with the second outer thread of the screw.

The tissue protection sleeve is a kind of a lengthening piece, which may be suitable to facilitate the introduction of the screw into a bone, wherein muscles or other tissue surrounding the bone will complicate the attachment of an augmentation tool directly at the proximal end of the screw.

With two separate elements, i.e., the sleeve and the driver, each engaging directly at the proximal (head) end of the screw, it is possible to apply forces in different directions precisely onto the screw, so that the screw may be positioned accurately at an appropriate site. With the driver, forces in circumferential direction may be applied to screw in (or out for explanation) the screw. With the sleeve, forces in an axial or a radial direction may be applied to the screw. As another advantage, the screw may be held in place by the screw driver while the tissue protection sleeve is loosened and removed from the proximal end of the screw.

A screw insertion system includes a screw having a leading end having a threaded shaft and a head at a trailing end. The head has a first diameter at a free end and a second diameter at an end connected to the threaded shaft. The first diameter being less than the second diameter. The head has an outer surface with a plurality of external helical threads extending from the first to the second end thereof. The head also has a drive element located within the first diameter open to the free end of the head. A screw holder or sleeve is provided and has a through bore with a trailing end. An interior surface at the leading end of the screw holder has a helically threaded portion, the thread portion having a first diameter located towards the trailing end of the holder and a second diameter at the leading end of the holder. The second diameter is greater than the first diameter, the second diameter of the holder generally equal to the second diameter of the bone screw head. A screw driver extends through the tubular screw holder and is engagable with the drive element on the screw head.

The screw head preferably has a conical outer shape between the first and second diameter of the head, and the threaded portion of the interior surface of the screw holder threaded portion has a matching conical shape. The screw head may have a part-spherical distally facing outer shape between the first and second diameters of the head.

The external threads of the head and the interior threads of the screw holder preferably are at least partially rounded threads. The at least partially rounded threads have rounded roots and flattened crests. Preferably the threads on the head and on the screw holder are left-handed threads.

The screw driver has an outer diameter small enough to be received within the bore of the screw holder preferably with a close fit. Preferably the outer diameter of the screw holder does not exceed the second diameter of the screw head so that a smooth transition is formed. The drive element of the bone screw head may be an internal hex drive. The conical outer shape of the head preferably has an opening angle of about 20°. Other aspects of the present invention are obtained by a screw insertion system including a screw having a threaded shaft and a head connected to the threaded shaft. The head has a conically tapered outer surface. The tapered surface increasing in distance from a central longitudinal axis of the screw from a free end of the head towards a larger diameter adjacent the connection between the head and the threaded shaft. The conically tapered head outer surface has at least two helically extending partially rounded threads. The screw head also has a recessed drive element open to the free end of the head. A tubular screw holder is provided having an outer surface and internal bore extending between a leading end and a trailing end for receiving the screw. The leading end has a conically tapered inner threaded portion for engaging the conically tapered outer thread of the screw head. The tubular screw holder outer surface having a diameter less than the maximum diameter of the conically tapered head. A screw driver is provided extending through the base in the tubular screw holder for engaging the recessed drive element in the screw head. Preferably, the threads on the head and on the screw holder are left-handed threads.

The system of the present invention includes a bone fastener. Preferably the bone fastener has a shaft at a leading end and a head connected to the shaft at a trailing end. The head having a first diameter at a free end and a second diameter at an end connected to the shaft. The first diameter is less than the second diameter with, the head having an outer surface extending between the first and second diameter. The head outer surface comprising a plurality of helical threads extending around the outer surface. Preferably each thread has curved flanks and a curved root intermediate the curved flanks with the threads having a flat crest on the outer surface of the head extending between adjacent curved flanks forming the thread.

The bone fastener shaft has a threaded portion at the leading end and the head outer surface has a conical shape. The conical shape of the head preferably has an opening angle of 18° to 22°. Preferably the threads on the head are left-hand threads, and are double or triple lead threads.

BRIEF DESCRIPTION OF THE DRAWINGS

FIG. 1 is a cross-sectional view of the bone screw insertion system of the presentation invention showing a bone screw, a tissue protection sleeve, and a screw driver;

FIG. 2A is a side view of the screw of FIG. 2;

DETAILED DESCRIPTION

Figure 1A:
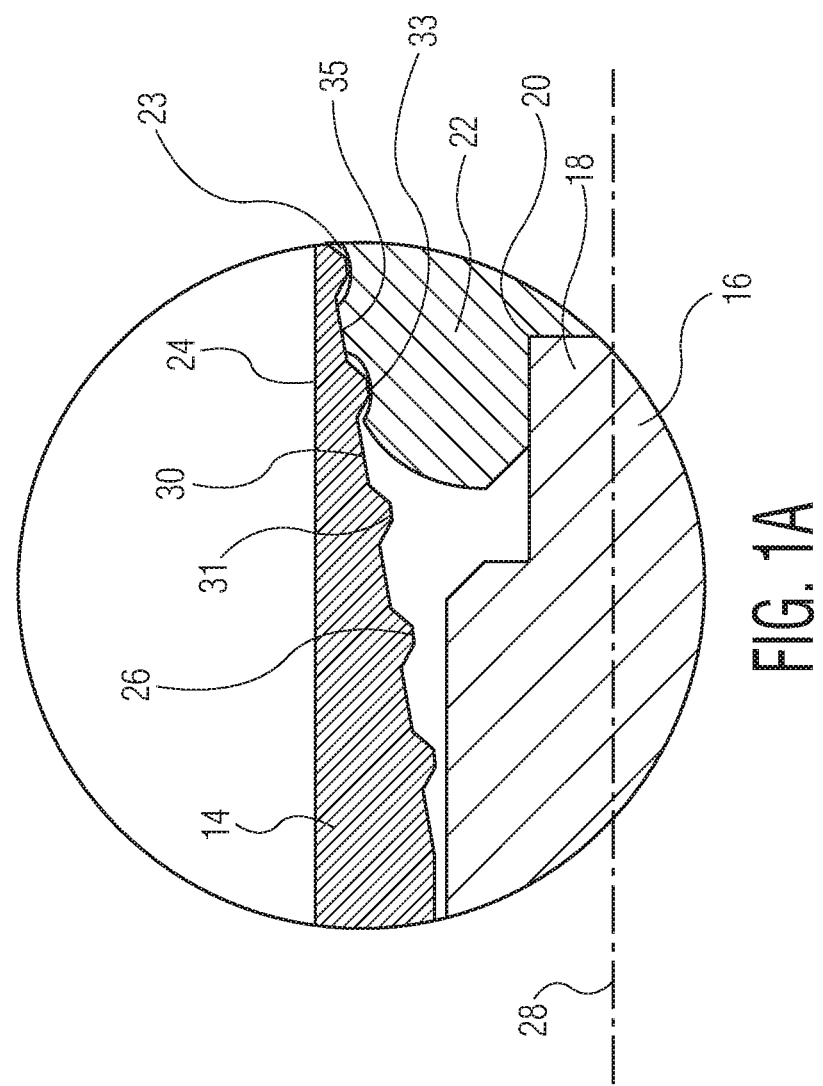
FIG. 1A is an enlarged view of the coupling between the tissue protection sleeve, bone screw head, and screw driver of the present invention as shown in FIG. 1.

Referring to FIG. 1 there is shown the screw insertion system of the present invention generally denoted as 10. The screw insertion system includes a screw 12, a sleeve or holder 14 for connecting to screw 12, and a driver 16 with shaft 17. In the preferred embodiment screw 12 is a bone screw, and sleeve 14 is a tissue protection sleeve used for inserting the threaded screw into a bone plate or bone nail (not shown). Driver 16 can be any standard screw driver having a leading distal end with a standard screw drive 18, such as a hex drive or a Torx® drive. Drive 18 is adapted to engage a socket or recess 20 in a head 22 of screw 12. Preferably screw 12 has a head 22 with threads 23 and a threaded shaft 25. Head 32 is adapted engage the threads 26 of internal surface 24 at a distal end of tissue protection sleeve 14. Threads 23 taper inwardly on moving away in a proximal direction from the bone screw threads on shaft 25.

Referring to FIG. 1A there is an enlarged view of the engagement between tissue protection sleeve 14, screw head 22, driver 16 and socket 20. It can be seen from FIG. 1A that the distal end 24 of sleeve 14 includes a plurality of threads along a threaded inner diameter 26. At the distal end 24 inner diameter threads 26 taper outwardly from central axis 28 of the bone screw sleeve 14 preferably in a conical manner. The distal threaded distal end inner surface 24 of sleeve 14 preferably includes flat root areas 30 and flat crests 31 along the outwardly tapered surface of inner surface 26 of sleeve 14. Screw head 22 has rounded roots 33 and flat crests 35. The outer diameter 27 at the leading end of the sleeve is substantially equal to the largest thread diameter of head 22 which is located adjacent to shaft 25. While the diameters do not have to be exactly equal a large step is to be avoided so that surrounding tissue is not irritated during insertion.

Figure 2:
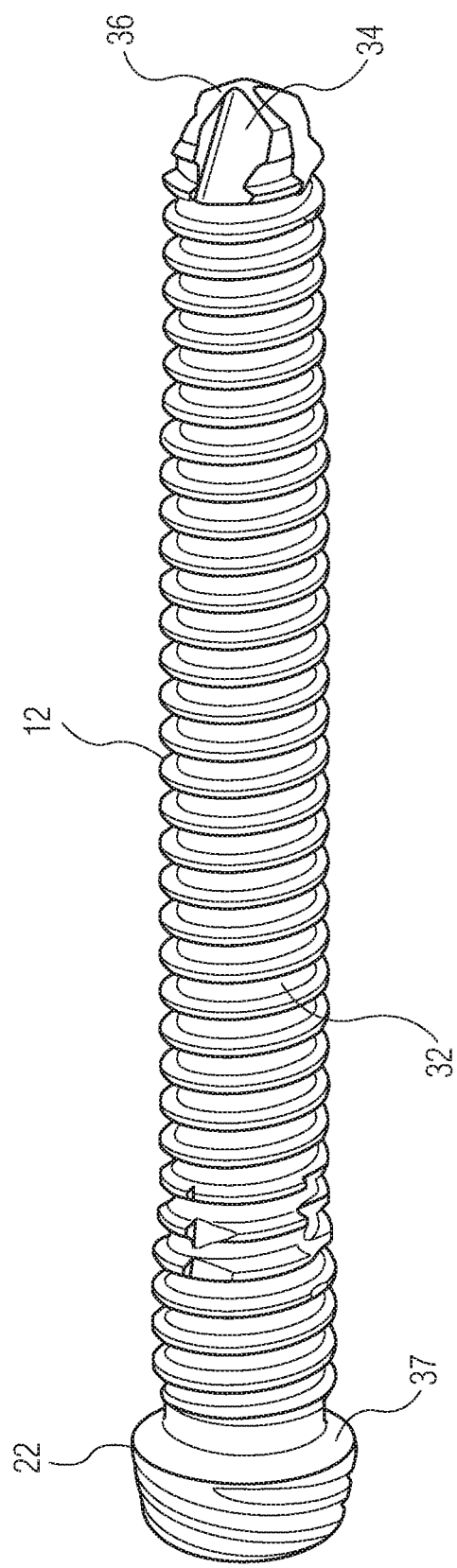
FIG. 2 is an isometric view of the bone screw of FIG. 1.

Referring to FIGS. 2 and 2A, there is shown bone screw 12 with head 22 and shaft 25 with threads 32. The threads 32 of bone screw 12 include a helical thread adapted to engage bone and may or may not have a self-drilling feature 34 adjacent a distal tip 36. The threads 32 of bone screw 12 may be any typical threads used for bone screws. A transition area 37 extends between the head 22 and shaft 25.

Sleeve 14 has an inner diameter 52 which receives an outer surface of driver shaft 17. These surfaces may be a close fit to permit sliding engagement.

Figure 3:
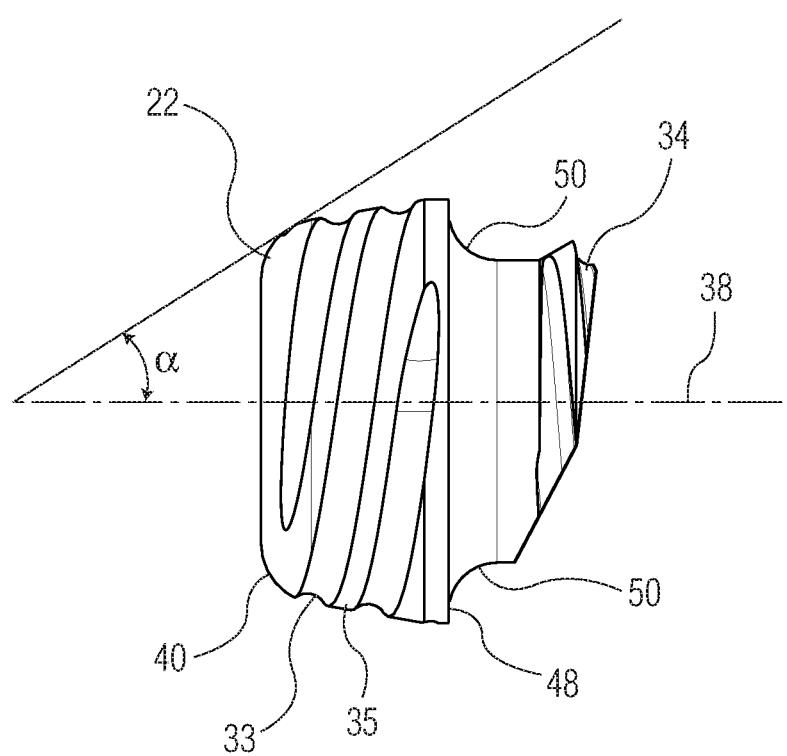
FIG. 3 is a view of the threaded head of the bone screw of FIG. 2.

Referring to FIG. 3, there is shown an enlarged view of head 22 which tapers outwardly from central axis 28 at an angle α. Angle α is preferably 9 to 10° thus making the cone angle of the tapering head 18 to 20°. The head 22 includes helical thread 40 which preferably has an arcuate root-shape 33 separated by a flattened crest 35 as best shown in FIG. 1A. The root 33 may have a circular shape of, for example, a radius of 0.6 to 0.8 mm. The threaded depth from the crest 35 to the bottom of the root 33 may be, for example, 0.14 mm. The threads are preferably a double or triple lead thread, and are left-handed, whereas, the threads of the bone screw shaft are right-handed. As shown in FIG. 3, the head has an annular surface 48 facing the distal end of the screw (i.e. towards tip 36)

Figure 4:
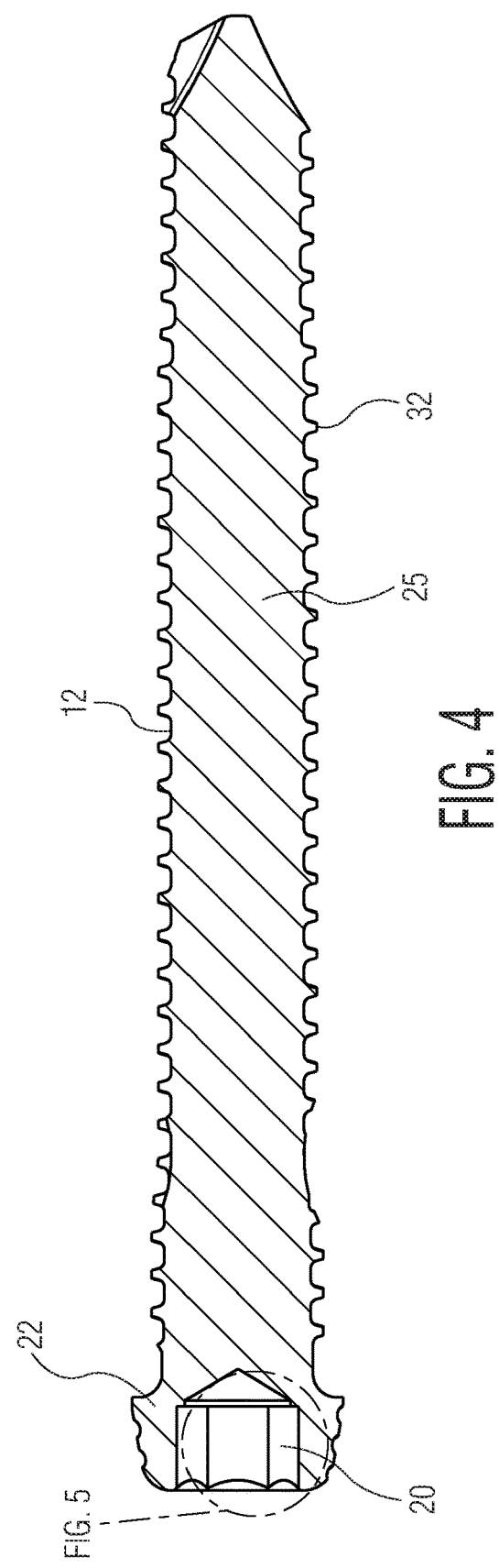
FIG. 4 is a cross-sectional view of the bone screw of FIG. 2.
Figure 5:
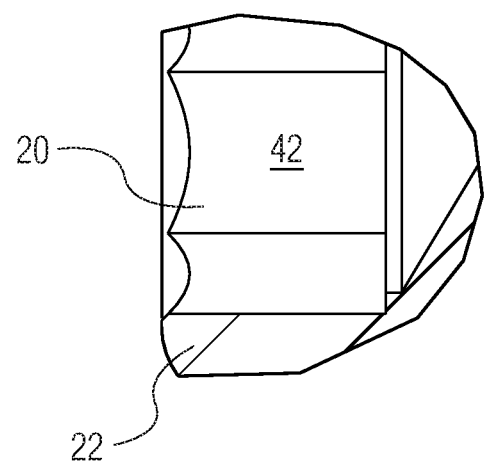
FIG. 5 is an enlarged view of the hex drive of the bone screw of FIG. 2.

Referring to FIGS. 4 and 5, there is shown a cross-section of bone screw 12 including the bone screw shaft 25 and in particular head 22, which includes a hex socket 20 for receiving the drive end 18 of the screw driver 16. FIG. 5 shows the flat sides 42 of hex socket 20. Socket 20, as shown, is adapted to receive a standard hex drive from an Allen wrench or screw driver. A TORX® drive or other polygonal drive could be used.

Figure 6:
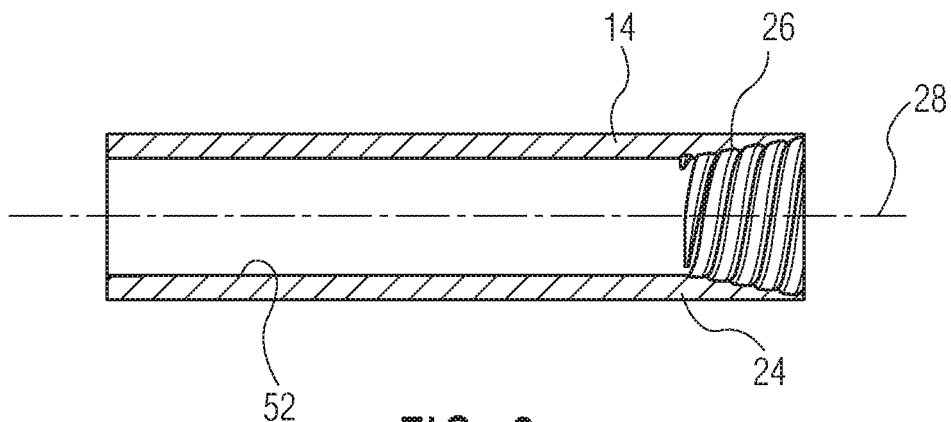
FIG. 6 is a cross-sectional view of the tissue protection sleeve of the present invention.
Figure 7:
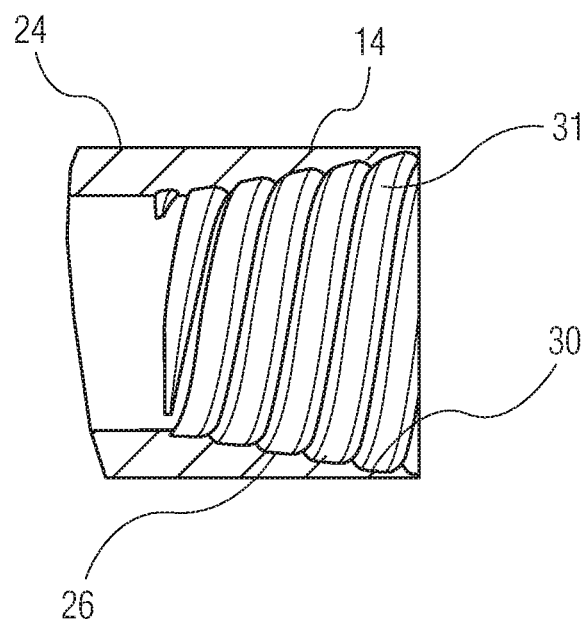
FIG. 7 is an enlarged view of the distal end of the tissue protection sleeve of the present invention.

Referring to FIGS. 6 and 7 there is shown tissue protection sleeve 14 including threaded distal end 24 including threaded inner diameter 26, which tapers outwardly from centerline 28. Threaded diameter 26 tapers outwardly at the same angle that screw threads 23 are tapered inwardly towards the head free end i.e., for example, 10°. Thus, the entire distal opening of the sleeve tapers outwardly on moving distally at an included angle of 20°. In order to more easily engage and disengage from head 22 of screw 12, the threads 26, as shown in FIG. 1A, have flat crests and flat roots. The crests are spaced such that they engage the deepest root area of circular or arcuate threads 33. These thread shapes produce less friction so that the tissue protection sleeve may be more easily removed from the head of the screw after implantation.

Referring to FIG. 3, in the preferred embodiment, head 22 includes a distally facing surface 37 which in FIG. 4 is annular planar surface 48. Surface 48 may be connected to screw shaft 25 by an arcuate portion 50 which, in the preferred embodiment, is concave. However, this connection portion 50 could be convex and have a part-spherical shape around the entire circumference of the junction between shaft 25 and screw head 22. This would allow for polyaxial movement of the screw as, for example, when implanted in a bone plate (not shown).

In use the surgeon threadably couples the sleeve or screw holder 14 to the head of 22 of screw 52 so that the outer diameter 27 is flush or nearly flush with the largest thread diameter of head 22. The surgeon then inserts the driver 16 through sleeve 14 into the drive 18 of screw 12. Screw 12 is then inserted into the bone. The sleeve 14 can be removed by rotating an exposed end of sleeve 14 in the direction of screw rotation because of the opposite left and right threads on the bone screw head 22 and shaft 25.

Figure 8A:
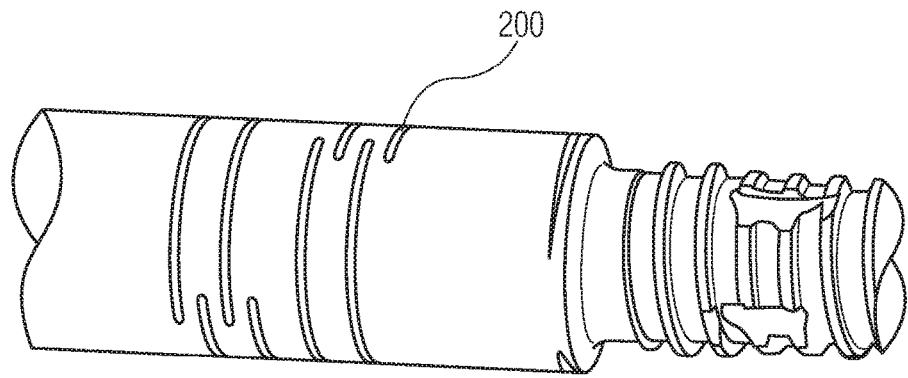
FIGS. 8A and 8B (in cross-section) show an alternate distal end for the tissue protection sleeve wherein the distal end of the sleeve can flex with respect to the axis of the bone screw.
Figure 8B:
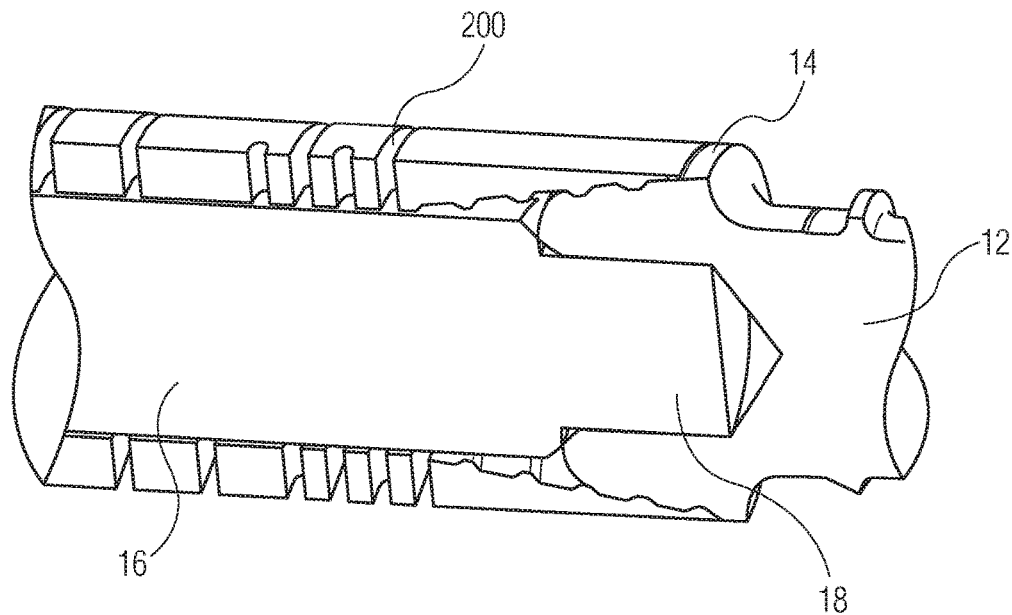

The sleeve may have a smaller outer diameter (OD), for example 7 mm and have markings near the grip which indicate when to stop turning, it may also have slotted structures to allow for "gripping" even when screws are inserted in a non-axial fashion. In other words, the distal end of sleeve 14 can flex slightly when the screw axis is angled with respect to the sleeve axis. Such structures are shown in U.S. Pat. No. 6,337,142, the disclosure of which is incorporated herein by reference. Such a structure is shown in FIGS. 8A and 8B which has a plurality of slots 200 spaced around the circumference of the tissue protection sleeve.

The sleeve may have a larger OD, for example 9 mm. The reason for the larger diameter of 9 mm is that especially for axially stable screws such a larger diameter increases the contact area between the tool tip and screw head which respectively improves the tactile sensation for the operator. This is important as the operator needs to know and feel when to stop turning (when the screw head hits the bone surface). With the larger diameter the sleeve distal end will be larger than the screw head diameter by 1 to 2 mm.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A screw insertion system comprising:
   a screw having a threaded shaft at a leading end and a head at a trailing end, the head having a threaded external surface extending from a first end to a second end thereof, the head having a first diameter at the first end and a second diameter at the second end connected to the threaded shaft, each of the first diameter and the second diameter being measured at a root of a helical thread of the threaded external surface, the first diameter of the head being less than the second diameter of the head and the head having a drive element located within the first diameter open to the first end of the head;
   a screw holder having a through bore with a trailing end and a leading end, an interior surface at the leading end having a threaded portion, the threaded portion having a first diameter located towards the trailing end of the screw holder and a second diameter at the leading end of the screw holder, the second diameter of the screw holder greater than the first diameter of the screw holder, the second diameter of the screw holder generally equal to the second diameter of the head; and
   a driver extending through the screw holder engagable with the drive element on the head.

2. The screw insertion system of claim 1, wherein the head has a conical outer shape between the first and second diameter of the head, and the threaded portion of the interior surface of the screw holder threaded portion has a matching conical shape.

3. The screw insertion system of claim 2, wherein the conical outer shape has an opening angle of about 20°.

4. The screw insertion system of claim 1, wherein the head has a part-spherical outer shape between the first and second diameters of the head.

5. The screw insertion system of claim 1, wherein the threaded external surface of the head includes external threads that are at least partially rounded threads and the threaded portion of the screw holder includes interior threads that are at least partially rounded threads.

6. The screw insertion system of claim 5, wherein the at least partially rounded threads have rounded roots and flattened crests.

7. The screw insertion system of claim 5, wherein the external threads on the head and the interior threads on the screw holder are left-handed threads.

8. The screw insertion system of claim 1, wherein the driver has an outer diameter being slidably received within the bore of the screw holder.

9. The screw insertion system of claim 1, wherein an outer diameter of the screw holder does not exceed the second diameter of the head.

10. The screw insertion system of claim 1, wherein the drive element of the head is an internal hex drive.

11. A screw insertion system comprising:
    a screw having a threaded shaft and a head connected to the threaded shaft, the head having a conically tapered outer surface increasing in distance from a central longitudinal axis of the screw from a free end of the head towards a larger diameter adjacent the connection between the head and the threaded shaft, the conically tapered outer surface having at least one helically extending partially rounded threads, the head having a recessed drive element open to the free end of the head; and
    a tubular screw holder having an outer surface and internal bore extending between a leading end and a trailing end for receiving the screw, the leading end having a conically tapered inner threaded portion for engaging the conically tapered outer thread of the head, the tubular screw holder outer surface having a diameter less than or equal to a maximum diameter of the conically tapered head.

12. The screw insertion system of claim 11, further comprising a driver extending through a base in the tubular screw holder for engaging the recessed drive element in the head.

13. The screw insertion system of claim 11, wherein the at least one partially rounded thread on the head and a thread of the conically tapered inner threaded portion on the screw holder are left-handed threads.

14. The screw insertion system of claim 11, wherein the recessed drive element of the head is an internal hex drive.

15. The screw insertion system of claim 11, wherein the at least one helically extending partially rounded thread has a rounded root and a flattened crests.

16. The screw insertion system of claim 11, wherein the conically tapered outer surface has an opening angle of about 20°.

17. The bone fastener of claim 16, wherein the at least one helically extending partially rounded thread on the head has curved flanks, a curved root intermediate the curved flanks, and a flat crest on the conically tapered outer surface of the head extending between adjacent curved flanks forming the at least one helically extending partially rounded thread.

18. A bone fastener comprising:
a threaded shaft at a leading end and a head connected to the shaft at a trailing end, the head having a threaded outer surface extending from a free end to an end connected to the shaft;
the head having a first diameter at the free end and a second diameter at the end connected to the shaft, each of the first diameter and the second diameter being measured at a root of a thread of the threaded outer surface, a crest adjacent to the second diameter being a maximum diameter of the bone fastener; and
the first diameter being less than the second diameter.

19. The bone fastener as claimed in claim 18, wherein the threaded shaft has a threaded portion at the leading end.

20. The bone fastener as claimed in claim 18, wherein the threaded outer surface on the head has a conical shape.

21. The bone fastener as claimed in claim 20, wherein the conical shape has an opening angle of 18° to 22°.

22. The bone fastener as claimed in claim 18, wherein the threaded outer surface of the head includes left-hand threads and the threaded shaft includes right-hand threads.

23. The bone fastener as claimed in claim 22, wherein the threaded outer surface of the head includes double or triple lead threads.

* * * * *